United States Patent [19]
Ginsberg

[11] 3,976,429
[45] Aug. 24, 1976

[54] BACKWASH SYSTEM FOR DILUTING APPARATUS

[75] Inventor: Guenter Ginsberg, Miami, Fla.

[73] Assignee: Coulter Electronics, Inc., Hialeah, Fla.

[22] Filed: Oct. 16, 1973

[21] Appl. No.: 406,788

[52] U.S. Cl............................. 23/259; 23/230 R; 23/253 R; 73/421 R; 73/421 B; 324/71 CP
[51] Int. Cl.²................ G01N 31/00; G01N 1/00; G01N 1/10
[58] Field of Search............. 23/259, 230 R, 253 R; 324/71 CP

[56] References Cited
UNITED STATES PATENTS

| | | | |
|---|---|---|---|
| 2,656,508 | 10/1953 | Coulter | 324/71 CP |
| 3,549,994 | 12/1970 | Rothermel et al. | 23/230 B |
| 3,567,390 | 3/1971 | Rothermel | 23/259 |
| 3,649,204 | 3/1972 | Farr | 23/259 |
| 3,759,667 | 9/1973 | Bannister et al. | 23/259 |
| 3,776,700 | 12/1973 | Gallant | 23/259 |

*Primary Examiner*—Morris O. Wolk
*Assistant Examiner*—Dale Lovercheck
*Attorney, Agent, or Firm*—Silverman & Cass, Ltd.

[57] ABSTRACT

A backwash system including a dispensing cylinder and valve arrangement for directing diluent as a backwash from a source to a sampling valve utilized to make dilutions thence to a sampler in the form of an aspirator tube. The sampling is performed by means of the aspirator tube introduced into a fluid for sampling and a vessel is provided for catching the backwash fluid and aspirating same to waste. The vessel and the tube are positioned relatively to enable the backwash to be caught in the vessel only when diluent is dispensed as backwash. The aspirator tube and collector vessel are returned to their normal relative condition either by movement of the tube relative to the collector vessel or vice versa. Suitable controls are provided to assure that backwash occurs only when the tube and vessel are conditioned to receive same.

7 Claims, 4 Drawing Figures

BACKWASH SYSTEM FOR DILUTING APPARATUS

BACKGROUND OF THE INVENTION

1. Field of the Invention

This invention relates generally to apparatus which utilizes vessels, valves and connecting conduits for the intermixing and/or diluting of fluids primarily for the purpose of making measurements and tests upon said fluids. More particularly, this invention is concerned with the type of automatic analysis instrument such as disclosed in U.S. Pat. Nos. 3,549,994 and 3,567,390 which employ the Coulter particle analyzing principle disclosed in U.S. Pat. No. 2,656,508, and provides herein backwash means to assure sample integrity in the operation of such and like apparatus.

2. DESCRIPTION OF PRIOR ART

In recent years so-called automatic chemistry apparatus has become popular, especially where testing and measurements are to be performed on a continuous basis, with many tests to be made simultaneously and complex routines to be repeated, but with different samples. One such apparatus is disclosed in U.S. Pat. No. 3,549,994 and is primarily intended for the measurement of parameters of blood.

In that apparatus, samples of whole blood are introduced in succession, and the apparatus performs the requisite dilutions, tests and computations needed for obtaining such information as white and red cell count, hematocrit, hemoglobin measurement, etc. In the course of performing such determinations, necessary sample suspensions of predetermined concentration are prepared within the apparatus and transferred between vessels thereof. Multiple dilutions, mixing, pumping, transfer and moving of fluids between vessels are accomplished within the systems on an automatic or programmed basis and are effected by means of suitable valving apparatus as described in said U.S. Pat. No. 3,549,994 and particularly, an advantageous valving apparatus being that disclosed in U.S. Pat. No. 3,567,390.

In such systems, one can automatically produce one or more sample suspensions from a first fluid specimen, while simultaneously commencing dilution of the first of a second fluid specimen before the desired dilutions of the first are completed, the system employs a transfer valve structure wherein a fluid sample is drawn into a first portion of the valve. The valve then is indexed to subtend a precise amount of the sample and to mix same with a known quantity of diluent to provide a first fluid suspension of known concentration which is directed to a station. At the same time, the first diluted fluid suspension from the immediately preceding original sample, and at the said station, is drawn or "thiefed" into a second portion of the valve apparatus so that upon indexing of the valve back to its initial or start position, a precise amount of the last-mentioned suspension is subtended and mixed with a second volume of diluent to produce a second diluted fluid suspension of determinable concentration which is directed to another station.

The fluid sample is obtained by dipping an aspirator tube or snorkel into a sample contained in a suitable vessel and a quantity thereof is drawn into the transfer valve.

It must be understood that the entire apparatus is fluid filled and that transfers of fluid units are carried out hydraulically under selective applications of fluid pressure and vacuum in accord with a prearranged program.

As previously stated, an aspirator tube, snorkel or other thief apparatus generally operated in accordance with programmed alternating pressure-vacuum operations is utilized for sample pickup. In the course of such and further operations, sample blood remaining in the aspirator tube, line or valving is subjected to clearance only by the action of the greater volume of the next succeeding sample. Accordingly, some residual sample was mixed with the next sample. This is called "carry-over" and is an undesirable occurrence. If the samples were from the same patient source, perhaps deleterious results may not follow. Generally, the first few runs after change of sample are required to be discarded due to such carry-over from one sample to another. Notwithstanding the similarity of the succession of samples, differences in character and viscosity, for example, may prevent a succeeding sample from clearing the earlier sample from the aspirator tube, fluid line, valve, etc., thus mixing and contamination may be encountered.

Means for clearing the aspirator tube of residual fluid and yet capable of being controlled by the program of the system as a whole would be desirable but as yet, have not been available.

SUMMARY OF THE INVENTION

A backwash system for coupling operationally into a fluid transfer and diluting system of the character described which is capable of clearing both aspirator tube, fluid lines and the sampling valve of the fluid transfer and diluting system comprising a source of diluent, selectively operable valve means, a receiving or collector vessel, means for effecting relative movement of said receiving vessel and aspirator tube and means for effecting transfer of said diluent from its source to said aspirator tube by way of said transfer valve means in a predetermined time relationship to the operation of the transfer valve means, and means positioning said receiving vessel in diluent receiving disposition when said diluent is backwashed through said valve and tube.

DESCRIPTION OF PREFERRED EMBODIMENTS

Figure 1:
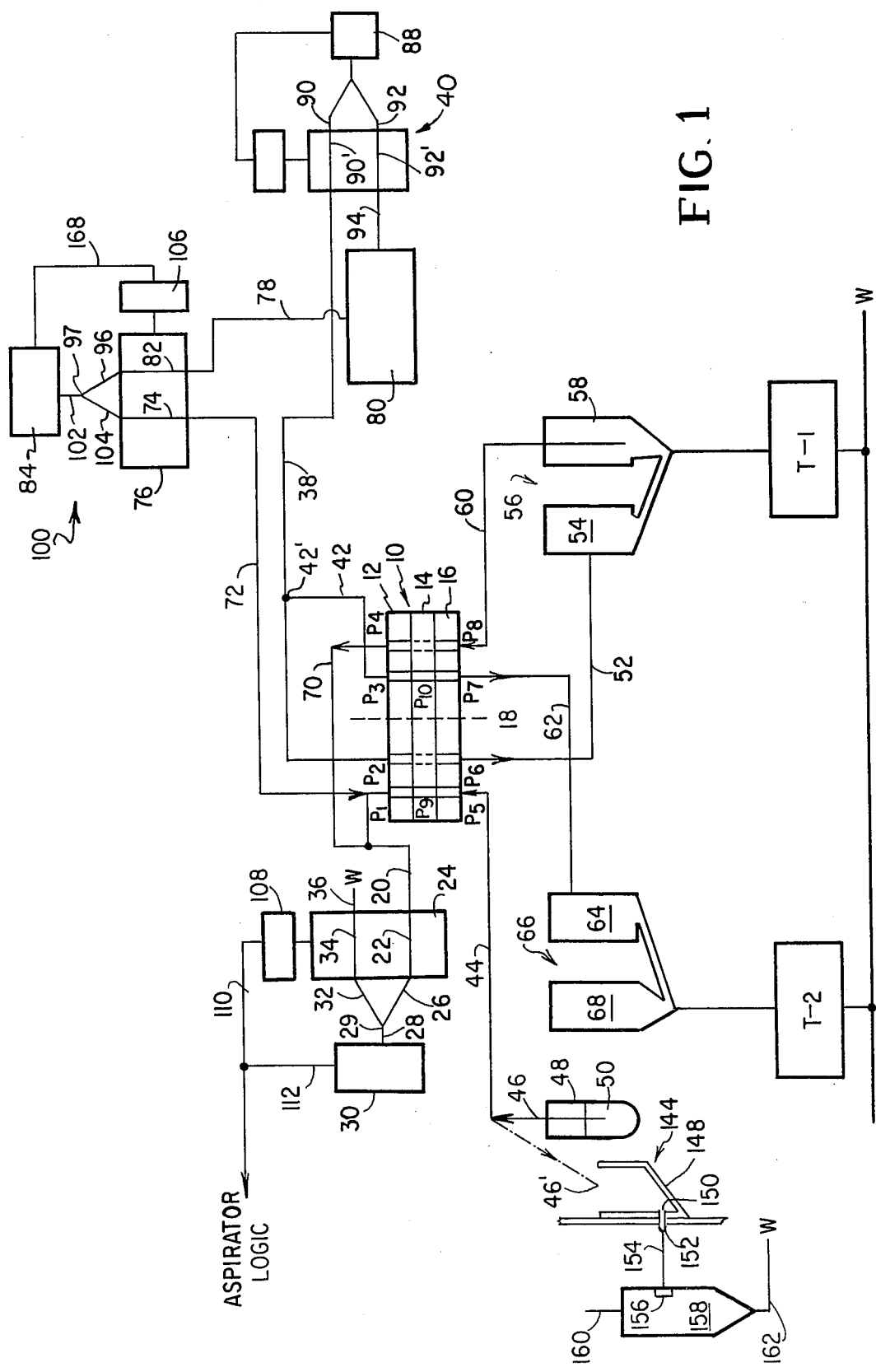
FIG. 1 is a schematic block or flow diagram of a diluting system adapted to be coupled with testing apparatus and including the backwash system of the invention.

At the outset it would be convenient to outline the general scheme of the system of the invention by explaining the functions which are performed.

A fluid sample is obtained in any convenient manner.
A fluid sample is obtained in any convenient manner.
A tube or snorkel, which shall hereinafter be referred to as the aspirator tube, is introduced into the sample and a quantity of the sample is drawn into a first portion of the fluid transfer valve of the system. The valve operates to segment a minute measured part of the sample therein and such part is diluted with a predetermined quantity of diluent. The resulting suspension is transferred with the added diluent then to first testing apparatus of the system wherein one or more tests or operations can be performed thereon. A portion of the first diluted solution from a previous sample simultaneously is drawn into another portion of the transfer valve as the sample is drawn into the transfer valve. Return of the valve to its initiate position causes the segmenting of the minute measured part of the first diluted solution and a second dilution is performed thereon by transferring that last part to a second testing apparatus, where remaining tests are performed. Making and transfer of the second dilution occurs simultaneous with the return of the transfer valve to its initial position.

A detailed description and explanation of the structure and operation of diluting systems of the type described as well as the combination therewith, of testing apparatus operating on the Coulter principle is set forth in said U.S. Pat. Nos. 3,549, 994; 3,567,390; and others. Principally, reference is made to U.S. Pat. Nos. 3,549,994 and 3,567,390 and each is hereby incorporated by reference herein as a part hereof.

In the system described in these patents, the sample consisted of whole blood. The blood sample tended to remain in the aspirator tube, and in the sample receiving portion of the transfer valve. Removal thereof from the aspirator tube was dependent upon the great volume of the next sample acting as a flushing agent. Additionally, the fluid transfer valve also required flushing to free same from the residual portions of the older sample whereby to prevent partial mixing or carry-over of successive samples. Obviously, carry-over of a part of a preceding sample will result in chance of error, particularly if there is much difference in characteristics between samples. No arrangement was heretofore provided to cleanse both valve and aspirator tubes of residual sample.

Accordingly, as will be described hereinafter, the invention herein is directed to providing means for backwashing diluent in premeasured quantities through the fluid transfer valve and the aspirator tube in a predetermined time relationship relative to the programmed operations of the apparatus, and, likewise, to coordinate means for collecting the backwash and disposing of same with the backwashing operation.

Means are provided, alternatively to backflow diluent through the sample receiving passage of the fluid transfer valve to the aspirator tube which is utilized for sample intake. Coordinated with such operation, a waste collector vessel is arranged for placement in a disposition whereat it is capable of receiving the backwash from the aspirator tube although normally such collector is not so disposed. One embodiment concerned provides a pivotally mounted collector vessel mounted on a spring biased shaft. The vessel is caused to pivot at the time when the backwash is effected. An aspirator is coupled to the vessel to direct the collected fluid to waste.

Another embodiment selectively rotates the aspirator tube between a normal sample taking condition and an angled condition when discharge therefrom is directed to a fixed positioned vessel. From there the backwash thus collected is aspirated to waste.

In FIG. 1 there is a diluting system schematically illustrated similar to the system illustrated and described in U.S. Pat. No. 3,567,390. The control or fluid transfer valve provided for the careful measurement of the sample is designated generally by the reference character 10. Valve 10 is formed of three elements, an intermediate or center element 14 movable with respect to stationary outer elements 12 and 16. The elements 12, 14 and 16 are arranged coaxially. The sandwiched or central element 14 is a carefully made and highly accurate structure having conduits P-9 and P-10, each on opposite sides of a central axis about which it is adapted to rotate. Each of these conduits is designed to carry a precise quantity or volume of some fluid, and upon movement between positions, there being two such positions, will slice off or subtend within itself the said volume of fluid and pass it or transfer it. This function is represented by the arrows showing the alignment of the conduits P9 and P10 with others carried by the stationary sandwiching members 12 and 16 of the valve 10. Although represented in the figure as a block or rectangular configuration, the valve 10 consisting of the elements 12, 14 and 16 preferably is cylindrical in configuration in accordance with and embodying the features of the valve illustrated specifically in FIGS. 6 – 10 of U.S. Pat. No. 3,567,390. The fluid transfer operation of valve 10 herein shall be described by reference only to the fluid passage means defined in the valve by which the transfer is effected and the respective dilutions made, schematically shown in rectangular configuration.

Each of the outer member 12 and 16 are fixed relative to one another and each is provided with two pairs of ports or passageways. These are designated P1, P2, P3 and P4 in element 12 and P5, P6, P7, and P8 in element 16. When the center element 14 is in one position, say the first position, the left-hand conduit or passageway P9 is aligned with the passageways P1 and P5 at the same time that the right-hand conduit or passageway P10 is aligned with the passageways P3 and P7. Rotation of the center element 14 brings the passageways P9 and P10 to the positions represented by the broken lines. Further flow between the passageways P1 and P5 is blocked as is further flow between the passageways P3 and P7. The passageway P9 is aligned with passageways P2 and P6 and the passageway P10 is aligned with passageways P4 and P8.

This action is reversible, and its effect is to slice or subtend a precise volume of fluid out of the one path and enable it to be inserted into the other path while blocking off the first path. This is done at both positions of the transfer valve 10.

As illustrated, various fluid lines connect the valve assembly 10 with the other elements of the system and for purposes of reference they are as follows:

Fluid line 20 connects from the passageway P1 to the normally closed conduit 22 of pneumatically operated pinch valve 24, functionally equivalent in the illustrated system to the sample control valve to which reference is made in Patent No. 3,567,390. Conduit 26 leads by way of line 28 to the sample pump which can be in the form of a diaphragmtype pump or, as illustrated, an aspirator cylinder 30. If a diaphragm type or other positive displacement pump is used, there is a lead to a source of alternating vacuum and pressure for operating the pump. Line 32 of Y connection 29 leads to normally open conduit 34 of pinch valve 24. Conduit 34 is coupled to waste W by line 36.

Fluid line 38 connects from the passageway P2 to the upper end of the diluent pinch valve 40.

Fluid line 42 connects from the passageway P3 to the fluid line 38 at point 42.'

Fluid line 44 connects from the passageway P5 to the sample aspirator tube 46. Note that the tube 46 is shown dipping into a vessel 48 containing a liquid sample 50, which here is whole blood. The vessel 48 is of any suitable construction and is withdrawn or otherwise removed when the requisite quantity of sample 50 has been withdrawn.

Fluid line 52 connects from the passageway P6 to chamber 54 of mixing vessel 56.

Fluid line 60 connects from the chamber 58 of mixing vessel 56 to the passageway P8 and is sometimes called a thief.

Fluid line 62 connects from the passageway P7 to the chamber 64 of mixing vessel 66, which includes a second chamber 68.

Fluid line 70 connects from the passageway P4 also to line 20 and to the normally closed conduit 22 of sample control pinch valve 24.

Fluid line 72 leads from the normally closed conduit line 74 of control valve 76.

Fluid line 78 leads from the diluent supply 80 to the normally open conduit 82 of the control valve 76. A pump in the form of a flexible diaphragm type or as here described a dispensing cylinder 84 having a chamber therein and operates to draw a selected quantity of diluent from supply 80 into the chamber of said cylinder 84 for storage and dispensing, e.g., the quantity preferably being 3 cubic centimeters.

Figure 2:
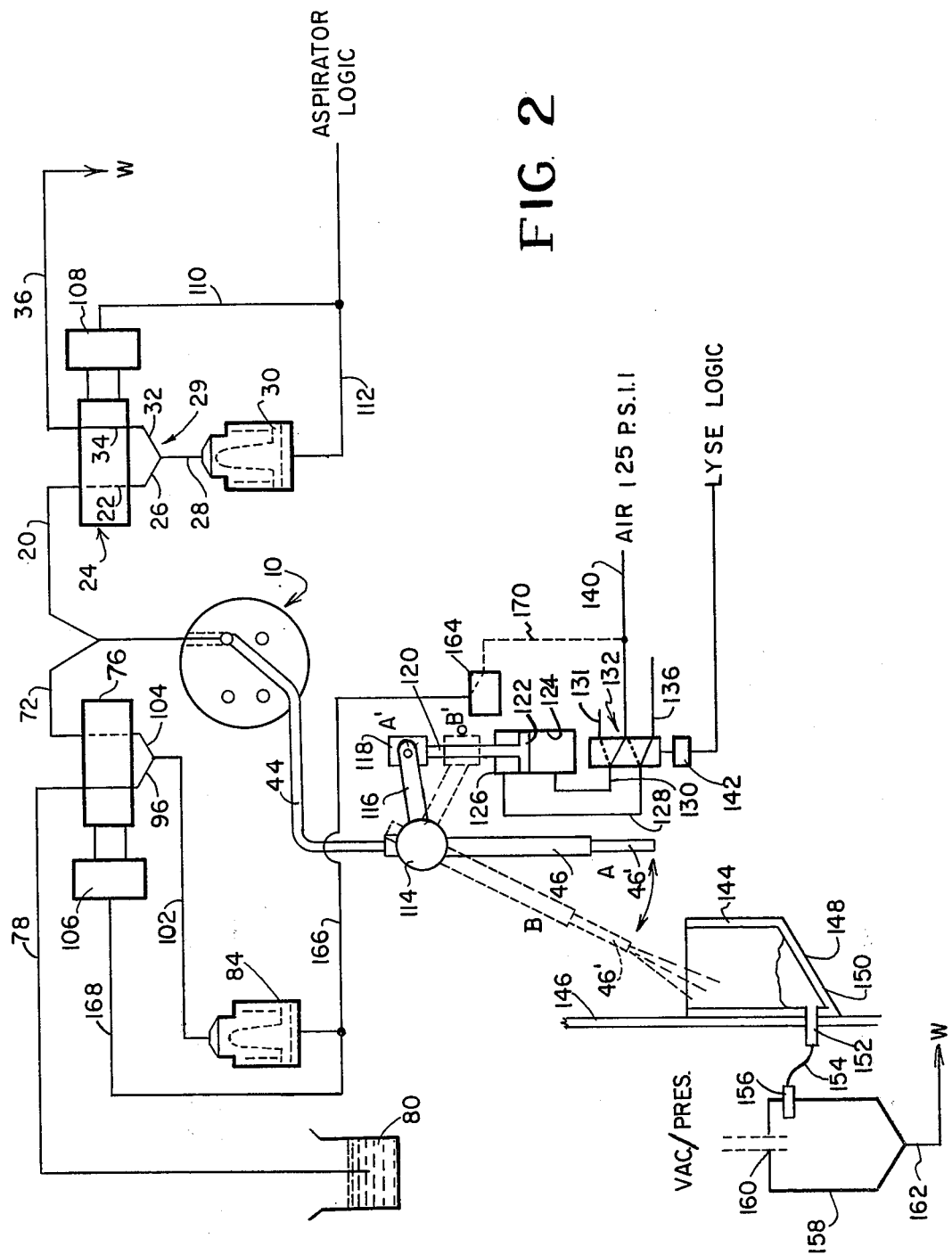
FIG. 2 is a more detailed schematic diagram of the backwash system utilized in the system of FIG. 1.

It will be noted in FIGS. 1 and 2 that aspirator cylinder 30 provided is functionally equivalent to the sample pump of the patented structure. The aspirator cylinder 30 is connected by line 26, 28 to conduit 22 and by lines 28, 32 to line 34 of the sample control valve 24. In the illustrated example, sample control valve 24 comprises a pneumatically controlled double pinch valve having an intermediate condition where both conduits 22 and 34 are closed before the normally closed conduit 22 is opened. This operational characteristic assures clean separation during the operation of the valve 24.

There also is a diluent control pump 88 connected by the lines 90 and 92 to the pinch valve 40. This arrangement may be identical to the equivalent arrangement described in the aforesaid pinch valve 24 and control valve 76. Accordingly, fluid line 38 is coupled to the normally closed conduit 90' of pinch valve 40. A fluid line 94 is coupled to the normally open conduit 92' from diluent supply 80. Fluid lines 90 and 92 form a Y connection into the diluent control pump 88.

The sample and diluent pumps may be of any construction, but preferably are manifolds having positive displacement means therein moving from end to end to displace a volume of fluid. Each pump draws into itself the same volume of fluid it is capable of pushing out.

The flexible diaphragm pump not shown suitable may differ from the equivalent pump of the patented system to include a flexible diaphragm pneumatically operated by a source of alternating vacuum and pressure. Such pump is formed of two chambers each having a port and separated by the flexible diaphragm. Introduction of pressure to one chamber forces the diaphragm fully into the other chamber and thus discharges any fluid contained therein. Application thereafter of vacuum will cause reversal of the flexible diaphragm and hence will result in introduction of fluid into the last vacated chamber. Cylinder pump 30 known as the aspirator cylinder pump 30 operates by reciprocable movement therein of its piston to draw and discharge fluid when actuated.

According to the invention herein, a backwash system generally designated by reference character 100 is provided and illustrated in more detail in FIG. 2. The system 100 is supplementary to the diluting system of the patented apparatus and is coupled operationally to the diluent supply 80. Line 78 leads from the diluent supply 80 to normally open conduit 82 of backwash fluid control valve 76. Conduit 82 is coupled to one arm 96 of a Y connection 97, with the leg 102 thereof connected to the chamber of piston-actuated storage cylinder dispenser 84. The other arm 104 of the Y connection 96 is coupled to normally closed conduit 74 of backwash control valve 76 and connects by way of line 72 to passageway P1 of fluid sample transfer valve 10.

Looking at FIG. 2, we note that both cylinderdispenser 30 and the actuator 108 of the valve 24 are coupled by way of lines 110 and line 112 respectively to the so-called aspirator logic for a period of time as described in the referenced U.S. Pat. No. 3,549,994. The normally closed conduit 22 of sample control valve 24 is coupled to line 26 of Y connection 29 while the other arm 32 thereof is coupled to the normally open conduit 34 of valve 24 and line 36 leading to waste generally represented by W. The leg 28 of Y connection 29 leads to the interior chamber of cylinder 30.

The aspirator tube 46 is mounted in a rotatable holder 114. Holder 114 has an outwardly extending arm 116 which is secured pivotally to a reciprocating head 118, itself secured at the upper end of plunger 120, as shown.

The opposite end of plunger 120 is secured to piston 122 within the interior chamber 124 of air cylinder 126. The interior chamber 124 of air cylinder 126 has ports opening thereinto on opposite sides of the piston 122, the ports being connected respectively by lines 128 and 130 to the outputs of four-way valve assembly 132. Four-way valve assembly 132 includes a pair of exhaust ports 134 and 136 and alternate paths leading to air line 140. The valve assembly 132 also includes actuator means 142 coupled to the lyse logic. Supply of air pressure by way of the valve 132 to one or the other side of the piston 122 causes the piston to reciprocate within the cylinder chamber 124. This in turn causes the head 118 to be raised or lowered between positions represented by A' and B'. Disposition of the head 118 at position B' causes the aspirator tube 46 to assume a canted condition B illustrated in broken line representation in FIG. 2.

The backwash dispenser cylinder 84 is operatively coupled to pilot actuator valve 164 by line 166, the actuator 106 of valve 76 is coupled by way of line 168 to line 166, and thus when cylinder 84 is operated to discharge its contents, the actuator 106 is operated to open the normally closed conduit 82. The actuator valve 164 is coupled to the line 140 by line 170 and operates when the head 118 is in the B' condition, in accordance with the operation of the lyse logic on the four-way valve 132.

In the canted condition B, the aspirator tube 46 is directed toward collector vessel 144 so that its tip 46' is over said vessel. The collector vessel 144 is secured to a panel 146 of the instrument and includes a tapered floor 148 to facilitate drainage. Port 150 formed in the vessel 144 is located near the floor 148 and is coupled by way of fitting 152 to line 1154. Line 154 is coupled by way of fitting 156 to a waste chamber 158. A source of alternating vacuum and pressure is applied to the waste chamber 158 as shown at 160 to aspirate the contents of vessel 144 and chamber 158 to waste, the latter by way of line 162 leading from the bottom of the chamber 158 to waste W.

Having explained the fluid lines and connections generally involved in the operation of the system concerned, it should be pointed out that the patented apparatus in which the backwash system of the invention operates, is completely programmed by a series of cams which are disposed in proper rotative disposition with respect to one another on shafts driven at a constant speed. The cams are simple switch actuators with cam surfaces that engage or disengage from the switches which are to be opened or closed in response to the movement of the cams. The switches may be electrical, or may be hydraulically or pneumatically operated valves. In the United States Patent No. 3,549,994 a chart is provided by means of which the timing is graphically illustrated by bars to explain which of the switches will be closed and opened by the cams and for what periods of time said cams are not illustrated in a drawing of this application.

Reference is made to said U.S. Pat. No. 3,549,994 for such chart and the description therein of the cams and their operation and timing. Three of the specific cam operations are important to the consideration of the operation of the backwash system of the invention in the environment of the general testing apparatus concerned herein and described in each of the referenced patents.

Of these timing operations, one concerns the operation involved in causing a whole blood sample to be drawn into the transfer valve 10 so that the portion disposed within passageway P9, for example, can be segmented and transferred to a vessel for mixing and testing. This operational logic shall be referred to herein as the aspirator logic and is operated by cam C2 of the patented system. At the same time that the aspirator logic initiates the operation of the aspirator cylinder and causes the sample valve actuator 108 to open the normally closed conduit 22 whereby to draw a volume of sample 50 from container 48, filling passageways P1, P9, and P5 of the valve 10, There is a predetermined volume of diluent transferred by means of the diluent control valve 40 and diluent pump 88 to the segmented diluted sample which had remained in passageway P10 from the previous operation. This so-called second dilution is led by line 42 to chamber 64 of the mixing vessel 66 for preparation of the second diluted sample upon which red blood cell determinations can be carried out in the appropriate testing apparatus T-2. At the same time as whole blood sample 50 is being drawn into the aligned passageways P1, P9 and P5, any liquid which may have been in the aspirator tube 46, the connecting fluid lines and aligned passageways of the valve to the aspirator the cylinder 30 are drawn ahead into the said cylinder. During the aspiration of sample 50, the aspirator tube 44 is in condition A, the piston 122 of the cylinder 126 being disposed in the A' condition.

Now, the sample transfer valve 10 is operated to rotate the intermediate or center portion 14 thereof, thereby subtending a known volume of sample within passageway P9. At the same time, passageway P10 is moved into alignment with passageways P4 and P8. The diluent pump 88 is activated controlled by valve 40 to drive a predetermined quantity of diluent from the diluent supply along line 38 to passageway P2, driving along therewith the plug or subtended sample portion from passageway P9 through passageway P6 along line 52 to the chamber 54 of mixing vessel 56 along with a predetermined quantity of diluent to form a first dilution of the sample. The end of the operation of cam to the aspirator logic, causes the valve 24 to reassume its normal position with conduit 34 open. The cylinder is operated to clear itself of its contents. The cylinder 30 operates to thief or draw a portion of the previous first dilution in the chamber 58 of the mixing vessel 56 by way of line 60 to the then aligned passageways P8, P10 and P4. At the same time that the first diluted sample is transferred from the mixing chamber to a lyse station at which shall be included here as a part of the testing apparatus T-1, the lyse logic operates, as explained in the reference patents when the first dilution is at the lysing station. Lysing agent is introduced to said first diluted sample at the lysing station just prior to its being passed into the actual testing chambers of testing apparatus T-1. At the time the lyse logic operates to initiate the lysing of the said first dilution is initiated. The four-way valve assembly 132 operates connecting line 128 to air pressure line 140 to introduce pressure into the chamber 124 of the air cylinder 156 above the piston 122, driving the piston 122 downwardly. Aspirator tube 46 rotates to position B, the tip 46' thereof pointing in the direction to discharge of backwash diluent to the collector vessel 144. When the head 118 engages pilot actuator valve 164, lines 166 and 168 are coupled by way of line 170 to line 140 and the backwash dispenser cylinder 84 is operated to drive its contents, that is a predetermined volume of diluent, e.g. say 3 cc, through the now open conduit 74 as the actuator 106 likewise is rendered operative to open said normally closed conduit and close the normally open conduit 82.

In the meantime, the center element 14 of valve 10 has been indexed back to its initial condition so that the volume of diluent flowing from the dispensing cylinder 84 along path following 102, 104, 74, and 72 respectively enters and passes through the passageways P1, P9 and P5. The backwash diluent continues from passageway P5 by way of line 44 to and through the aspirator tube 46. The lyse logic acts again to shift the 4-way valve 126 and introduce pressure to the portion of the chamber 124 of cylinder 126 which is below the piston 122. The piston 122 is driven upwardly and once again the aspirator tube 44 is placed in vertical or sample-taking condition and the system is ready for resampling, a new vessel 48 introduced. The aspirator logic operates to draw a new sample and the aspirator logic operates to drive the cylinder 30 contents and that of lines 32 and 34 to waste.

It should be understood that diluent will not be backwashed through the aspirator tube 44 until the said tube is in position B, this delay controlled by the pilot actuator valve 164.

Figure 3:
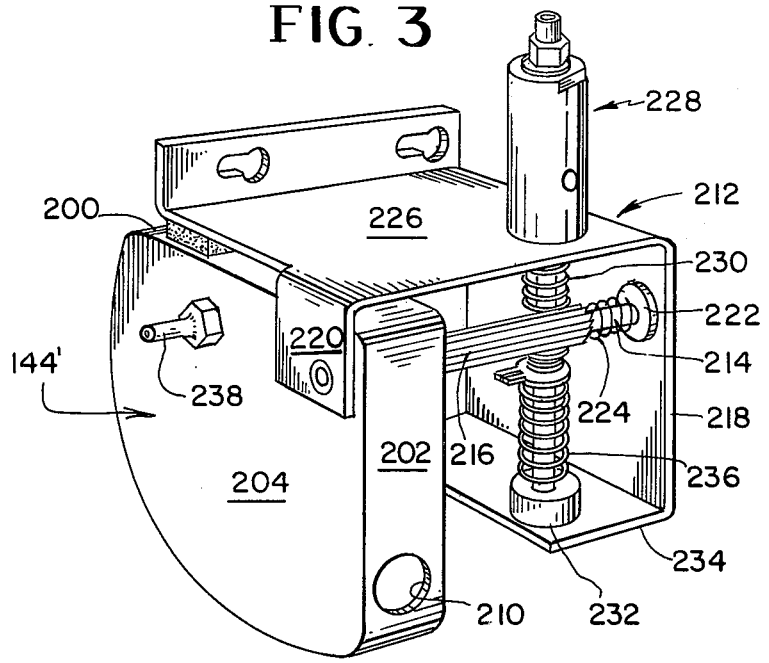
FIG. 3 is a perspective view of a form of collector vessel of a modified backwash system according to the invention.
Figure 4:
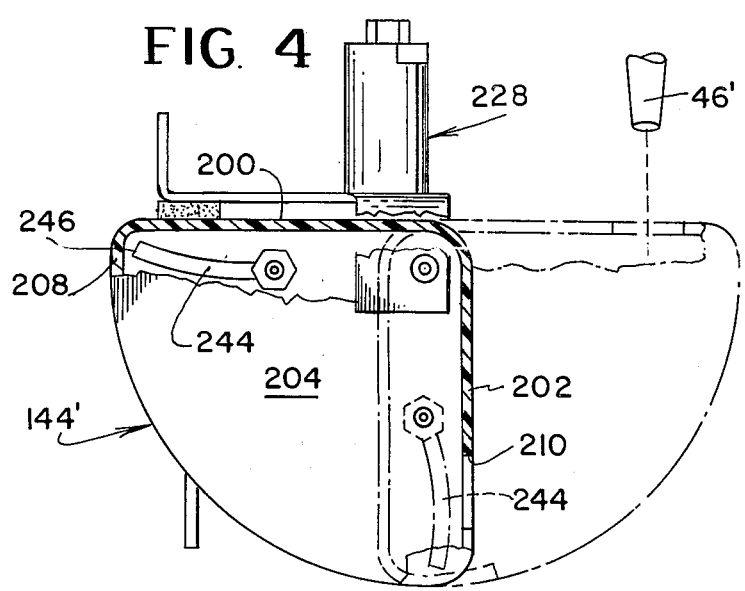
FIG. 4 is an elevational view of the collector vessel illustrated in FIG. 3, portions being removed to illustrate interior detail, and the phantom representation showing the vessel in collection condition.

In FIGS. 3 and 4 another embodiment of the invention is illustrated wherein the relative movement of aspirator tube 46 and collector vessel 144 is reversed, with the aspirator tube 46 being stationary, and the collector vessel 144' being pivotally mounted so that at the proper time, it may be placed in receiving condition immediately below the tip 46' of the aspirator tube 46 and backwashing may take place. The collector vessel 144' then is withdrawn out of the way at other times. The collector vessel 144' comprises a pie-shaped hollow vessel having first and second walls 200, 202 at right angle one to the other, side walls 204 and 206, and an arcuate connecting wall 208. Wall 202 is provided with a small circular opening or mouth 210. A mounting bracket 212 enables the collector to be positioned on the panel (not shown) of the instrument so that wall 202 is flush with the mouth of a suitable recess which can be provided on said panel. The vessel 144' is secured to a shaft 214 carrying pinion gear 216. The position of the collector 144' relative to the mounting flanges 218, 220 of the bracket 212 is fixed by coil spring 224 bearing against suitable washers 222. Bracket 212 includes a planar portion 236 from which mounting flanges 218, 220 depend. An air pressure operated cylinder 228 is mounted on the planar portion 226 and a reciprocal rack 230 extends outwardly from the cylinder 228 through portion 226 to terminate in cup 232 secured on the inside surface return bent flange 234 of bracket 212. Coil spring 236 is provided to bias the rack 230 toward the cylinder 228. The rack 230 and pinion gear 216 are coupled so that movement of the rack 230 against the spring bias of spring 236 will rotate pinion gear 216 causing the collector vessel 144' to pivot outward about its mounting axis and to present opening 210 to the tip 46' of aspirator tube 46 as shown in phantom outline, in FIG. 4. The working end of the cylinder 228 is coupled to the equivalent of line 140 operated through an equivalent of valve 132 to the lyse logic so that cylinder 226 operates to drive the collector vessel 144' to its receiving condition only when cylinder 84 and actuator 106 operates. An evacuation hose can be coupled to the exterior portion of plastic (tetrafluorethylene or the like) fitting 238 and an interior hose 244 is coupled to the interior end of the fitting. Hose 244 leads to the lower corner 246 of vessel 144' so as to reach all fluid contained therein when the collector vessel 14' is in its receiving condition.

What it is desired to secure by Letters Patent of the United States is:

1. A backwash system capable of being operationally coupled for use with a diluting system of the type providing a plurality of dilutions of differing concentration from a single fluid sample and which diluting system includes, a source of fluid sample and a source of diluent, a fluid transfer valve coupled to the sources and having first and second portions, the first portion for receiving and isolating therein an amount of the fluid sample, the first portion of said fluid transfer valve being capable of combining the amount of sample with a first volume of diluent by being in fluid flow communication with said diluent source to produce a precise desired first dilution, and the second portion capable of receiving and isolating therein an amount of the first dilution for making a second solution, an aspirator including an aspirator tube introducible into the fluid sample and coupled to the first portion; said backwash system arranged to pass diluent from the source thereof to the first portion of the fluid transfer valve and to and through the aspirator tube at a predetermined stage during operation of said system, said backwash system comprising, a pump having a chamber capable of storing and delivering a known volume of diluent, a first fluid conduit leading from the diluent source to said pump and a second fluid conduit leading from said pump to the fluid transfer valve, a valve including an actuator therefor positioned intermediate said first and second conduits and diluent source and fluid transfer valve respectively, the fluid transfer valve operable to control flow through said first and second conduits and between a first position only permitting passage of diluent from the diluent source to the pump and a second position only permitting passage of diluent from the pump to the fluid transfer valve, a collector vessel located to receive the backwash diluent from the aspirator tube, means for effecting relative movement of one of the aspirator tube and said collector vessel to cause said collector vessel to assume a backwash receiving condition with respect to the aspirator tube and a control mechanism operating to deliver diluent as backwash only when the collector vessel is in said backwash receiving condition.

2. The backwash system as claimed in claim 1 and a fluid pressure operated cylinder, a reciprocable plunger in said cylinder, a pilot actuator for said plunger, a pressure source, said plunger and said pilot actuator being coupled to said pressure source, movement of said plunger being effective to cause relative movement of the aspirator tube and collector vessel at the predetermined stage.

3. The backwash system according to claim 1 in which said collector vessel is moved and the aspirator tube is stationary.

4. The backwash system as claimed in claim 1 in which the aspirator tube is moved and said collective vessel remains stationary.

5. The backwash system as claimed in claim 2 in which the collector vessel comprises a hollow, segmentally configured vessel having an inlet opening in one wall thereof, said vessel being pivotally mounted for selective limited rotation about an axis taken through a corner thereof, a spring-biased rack and pinion arrangement coupled to said vessel for mounting said vessel in a normal condition with the inlet opening thereof nonaligned relative to the aspirator tube and said rack and pinion means operable to effect pivotal movement of said collector vessel about said axis to align said inlet opening with the aspirator tube for delivery of backwash diluent to said collector vessel.

6. The backwash system as claimed in claim 3 in which the aspirator tube is rotatively mounted movable between a position enabling sample intake and the backwash receiving condition where the aspirator tube is directed angularly toward said collector collector vessel.

7. The backwash system as claimed in claim 1 and a rotatable holder, the aspirator tube being arranged mounted to said rotatable holder in normally vertically oriented condition; a fluid pressure operated cylinder including a chamber, a piston reciprocal within said chamber, a plunger movable with said piston and extending from said cylinder, a linkage coupled between said holder and said plunger and pivotally secured to said plunger; and means for introducing fluid pressure to said cylinder to move said piston between a pair of positions, one of which causes angular disposition of the aspirator tube.

* * * * *

UNITED STATES PATENT AND TRADEMARK OFFICE
CERTIFICATE OF CORRECTION

PATENT NO. : 3,976,429
DATED : August 24, 1976
INVENTOR(S) : GUENTER GINSBERG

It is certified that error appears in the above-identified patent and that said Letters Patent are hereby corrected as shown below:

Col. 2, line 66, delete this line; col. 4, line 62, change "diaphigmtype" to --diaphragm-type--; col. 5, line 4, "42.'" should be --42'--; col. 6, line 21, change "cylinderdis" to --cylinder-dis--; col. 7, line 42, 43, delete "and is operated by cam C2 of the patented system"; col. 7, line 48, the comma "," should be a period --.--; col. 7, line 61, before "the cylinder" insert --of--; col. 8, line 10, delete "cam"; col. 8, line 29, change "156" to --126--; col. 9, line 16, change "236" to --226--; col. 9, line 40, change "14" to --1441--; col. 10, line 52, delete "collector", second occurrence Signed and Sealed this Twenty-sixth Day of April 1977

[SEAL]

Attest:

RUTH C. MASON
*Attesting Officer*

C. MARSHALL DANN
*Commissioner of Patents and Trademarks*